(12) United States Patent
Kalonia et al.

(10) Patent No.: US 7,630,076 B2
(45) Date of Patent: Dec. 8, 2009

(54) DUAL-DETECTOR SYSTEMS AND METHODS HAVING UTILITY IN BIOMOLECULAR MEASUREMENTS

(75) Inventors: Devendra S. Kalonia, Ashford, CT (US); Bajaj Harminder, Millbrae, CA (US); Sharma K. Vikas, Millbrae, CA (US)

(73) Assignee: University of Connecticut, Farmington, CT (US)

( * ) Notice: Subject to any disclaimer, the term of this patent is extended or adjusted under 35 U.S.C. 154(b) by 267 days.

(21) Appl. No.: 11/492,333

(22) Filed: Jul. 25, 2006

(65) Prior Publication Data
US 2007/0178013 A1    Aug. 2, 2007

Related U.S. Application Data

(60) Provisional application No. 60/702,410, filed on Jul. 26, 2005.

(51) Int. Cl.
*G01N 21/00* (2006.01)
(52) U.S. Cl. .................. 356/338; 356/340; 356/343
(58) Field of Classification Search ............... 356/337, 356/338, 339, 340, 343
See application file for complete search history.

(56) References Cited

U.S. PATENT DOCUMENTS

| | | | |
|---|---|---|---|
| 4,573,796 A * | 3/1986 | Martin et al. | ............... 356/318 |
| 4,616,927 A | 10/1986 | Philips et al. | |
| 4,693,602 A | 9/1987 | Wyatt et al. | |
| 4,952,055 A | 8/1990 | Wyatt | |
| 5,250,186 A | 10/1993 | Dollinger | |
| 5,269,937 A | 12/1993 | Dollinger | |
| 5,305,071 A | 4/1994 | Wyatt et al. | |
| 5,305,073 A | 4/1994 | Ford | |
| 5,530,540 A | 6/1996 | Wyatt et al. | |
| 5,676,830 A | 10/1997 | Janik et al. | |
| 5,734,464 A * | 3/1998 | Gibbs | ........................ 356/39 |
| 5,936,714 A * | 8/1999 | Gibbs | ........................ 356/39 |
| 6,315,955 B1 * | 11/2001 | Klein | ........................ 422/73 |
| 6,404,493 B1 | 6/2002 | Altendoft | |
| 6,411,383 B1 | 6/2002 | Wyatt et al. | |

(Continued)

OTHER PUBLICATIONS

Wen, et al., Size-Exclusion Chromatography With On-Line Light-Scattering, Absorbance, And Refractive Index Detectors For Studying Proteins And Their Interactions. *Anal. Biochem.* 240:155-166, 1996.

(Continued)

*Primary Examiner*—Roy Punnoose
(74) *Attorney, Agent, or Firm*—McCarter & English, LLP

(57) ABSTRACT

Apparatus, systems and methods for measurement of $B_{22}$ values of proteins in aqueous solutions in flow-mode utilize a dual-detector cell are provided. Simultaneous measurement of protein concentration and scattered light intensity is facilitated as the protein elutes from a size-exclusion column. Each data point on the resulting chromatograms is converted to Rayleigh's ratio, $R_\theta$, and to concentration c, respectively. The $B_{22}$ value is calculated from the slope of the Debye plot ($Kc/R_\theta$ versus c) generated from a range of the concentrations obtained from these chromatograms for a single protein injection. Measurements may be analyzed using modeling data derived from a predetermined modeling equation to quantify self-association of molecules. The apparatus and method provide a reliable means for determining $B_{22}$ values for such proteins as lysozyme, chymotrypsinogen, and chymotrypsin in various solution conditions.

20 Claims, 10 Drawing Sheets

U.S. PATENT DOCUMENTS

| | | | |
|---|---|---|---|
| 6,426,405 | B2 | 7/2002 | Jeng |
| 6,651,009 | B1 | 11/2003 | Trainoff et al. |
| 7,440,101 | B2 * | 10/2008 | Auer et al. .................. 356/338 |
| 2004/0067167 | A1 * | 4/2004 | Zhang et al. ............. 422/82.05 |
| 2005/0105077 | A1 * | 5/2005 | Padmanabhan et al. ....... 356/39 |
| 2005/0255600 | A1 * | 11/2005 | Padmanabhan et al. ....... 436/63 |
| 2007/0206203 | A1 * | 9/2007 | Trainer ...................... 356/521 |

OTHER PUBLICATIONS

Bloustine, et al., Measurements Of Protein-Protein Interactions By Size-Exclusion Chromatography, *Biophys. J.* 85:2619-2623, 2003.

Wyatt, Light Scattering And The Absolute Characterization Of Macromolecules. *Anal. Chim. Acta.* 272:1-40, 1993.

Wyatt, Mean Square Radius Of Molecules And Secondary Instrumental Broadening. *J. Chromatogr. A.* 648:27-32, 1993.

Bajaj, et al., Determination Of Second Virial Coefficient Of Proteins Using A Dual-Detector Cell For Simultaneous Measurement Of Scattered Light Intensity And Concentration In SEC-HPLC, Biophysical Journal, vol. 87, Dec. 2004, pp. 4048-4055.

Jackson, et al., Characterization Of Biopolymers Using A Multi-Angle Light Scattering Detector With Size-Exclusion Chromatography. *J. Applied Polym. Sci.* 43:99-114, 1989.

Netopilik, Combined Effect Of Interdetector Volume And Peak Spreading In Size Exclusion Chromatography With Dual Detection. *Polymers.* 38:127-130, 1997.

Netopilik, Problems Connected With Band-Broadening In Size-Exclusion Chromatography With Dual Detection. *J. Biochem. Biophys. Meth.* 56:79-93, 2003.

Wyatt, et al., The Interdetector Volume In Modern Light Scattering And High Performance Size-Exclusion Chromatography. *LC-GC.* 11:862-872, 1993.

Zammit, et al., Factors Influencing Detector Matching In Multidetector SEC: Solvent And Concentration Effects. *Polymers.* 39:5789-5798, 1998.

* cited by examiner

DUAL-DETECTOR SYSTEMS AND METHODS HAVING UTILITY IN BIOMOLECULAR MEASUREMENTS

CROSS-REFERENCE TO RELATED APPLICATIONS

The present application claims the benefit of a provisional patent application entitled "Dual-Detector Instrumentation Having Utility in Biomolecular Measurements," which was filed on Jul. 26, 2005 and assigned Ser. No. 60/702,410. The entire contents of the foregoing provisional patent application are incorporated herein by reference.

BACKGROUND

1. Technical Field

The present disclosure is directed to advantageous apparatus, systems and methods for obtaining desired measurements. More particularly, the present disclosure is directed to apparatus, systems and methods for measuring properties of biomolecules, e.g., proteins. The disclosed apparatus, systems and methods permit simultaneous measurement of scattered light intensities and concentration, e.g., using a single flow cell. Moreover, the disclosed apparatus, systems and methods permit accurate measurements to be made that support and/or facilitate calculation of the thermodynamic second viral coefficient of molecules, while simultaneously addressing issues associated with interdetector delay volume (IDV) and/or band-broadening. Exemplary embodiments of the present disclosure facilitate protein-related measurements using an advantageous dual-detector cell, and the dual-detector cell may be employed in the determination of the second viral coefficient of proteins in aqueous solutions.

2. Background Art

Protein-protein interactions play an important role in several phenomena of interest, including protein crystallization (George et al., 1997; George and Wilson, 1994), which relates to protein solubility (Guo et al., 1999; Rosenbaum and Zukoski, 1996), amorphous precipitation (Curtis et al., 2002; Piazza, 1999; Poon, 1997), formation of reversible protein aggregates in supersaturated solutions (Knezic et al., 2004), and irreversible aggregation (Chi et al., 2003a; Ho et al., 2003; Petsev et al., 2000; Zhang and Liu, 2003). These in turn have implications in the pathology of diseases, such as Alzheimer's (Fabian et al., 1993) and in the stability of protein pharmaceuticals (Chi et al., 2003b).

The second viral coefficient, $B_{22}$, which is a result of protein-protein interactions, represents non-ideality in dilute protein solutions (Tanford, 1961), and has been widely used as a parameter to study weak protein-protein interactions in aqueous solutions, e.g., to indicate whether the protein molecules (macromolecules, biomolecules) are experiencing a net attractive force or a net repulsive force. For example, correlation has been shown among $B_{22}$ values, solubility of proteins, and solution conditions under which protein crystals can be obtained (Guo et al., 1999).

Widespread application of $B_{22}$ values for investigating protein-protein interactions is lacking, presumably due to the limitations of the commonly employed techniques of batch-mode static light scattering, membrane osmometry, and sedimentation equilibrium. In addition to the long time durations necessary to complete these experiments (~1-2 days), these techniques require large amounts of protein (~25-100 mg) in order to obtain reliable estimates for $B_{22}$ values. Furthermore, errors can be introduced from impurities in the sample, such as dust particles or protein aggregates.

Recently, reports have emerged on rapid and improved methods to estimate protein-protein interactions in aqueous solutions, i.e., methods based either on self-interaction chromatography (Tessier et al., 2002) or size-exclusion chromatography (Bloustine et al., 2003). Although promising, these techniques require additional steps for determination of the $B_{22}$ values. The technique of self-interaction chromatography, for example, requires prior immobilization (Tessier et al., 2002) of the same protein; unfortunately, immobilization itself can affect protein structure and, hence, protein-protein interactions. Attempts to utilize size-exclusion chromatography (SEC) (Bloustine et al., 2003), which is routinely used in protein molecular weight characterization, have also been described for the measurement of protein-protein interactions. Bloustine et al. (2003) utilized the solute distribution coefficient as determined from the retention times in SEC to obtain the $B_{22}$ values of proteins in aqueous solutions, and Wyatt (2002) recently disclosed the use of SEC utilizing a light scattering detector and a concentration detector connected in series to obtain the $B_{22}$ values of proteins. Although this technique minimizes contributions from dust and aggregate impurities, it is still prone to errors arising from interdetector delay volume (IDV) and interdetector band broadening (Netopilik, 1997, 2003; Shortt, 1994; Wyatt, 1993b; Wyatt and Papazian, 1993; Zammit et al., 1998) within the two detectors, and hence requires mathematical correction factors to obtain the $B_{22}$ values.

The IDV and band broadening issues in SEC utilizing two detectors (i.e., a light scattering detector and a concentration detector, such as an ultraviolet detector) connected in series are significant, especially when discrete data points on the chromatogram, rather than the whole chromatogram, are used for analysis. When the protein sample, after separation in the SEC column, passes through the two detectors in series, a lag time occurs in the chromatogram due to physical separation of the detectors that relates to IDV. For proper analysis, the chromatograms from the two detectors must be overlaid precisely after correcting for this IDV. This is commonly attempted by measuring the peak-to-peak time difference between the two chromatograms, using a known standard and converting this time difference to the IDV from flow rate information. Once known, this IDV is then used for all samples. The IDV phenomenon is schematically represented in FIG. 1B, which is described in greater detail hereinafter.

U.S. Pat. No. 5,305,071 to Wyatt discloses a refractometer structure. The disclosed refractometer includes a capillary, is surrounded by detectors coplanar with the capillary, and is illuminated through the capillary by a light source, such that the angular variation of light scattered by particles flowing through the capillary is measured. A second light source and a displacement detector are incorporated into the apparatus such that the refractometer also functions as a concentration sensitive detector. According to the Wyatt '071 patent, the disclosed refractometer, when combined with the technique of size exclusion chromatography, will permit measurements of molecular size and weight of each separated fraction irrespective of the constancy of flow rate, since both light scattering and concentration measurement may be performed on the same flowing volume element of effluent. The Wyatt '071 patent further states that the disclosed refractometer, when used with another form of concentration detector, such as ultraviolet absorption or evaporative mass detection, will permit deduction of the differential refractive index increment dn/dc with concentration and that, in this manner, the physical parameters of co-polymers may be derived by combining the measurements of the differential refractometer, light scattering array, and concentration sensitive detector.

U.S. Pat. No. 6,404,493 to Altendorf discloses a dual large angle light scattering detection device/system with a configuration that is particularly suitable for use with planar liquid sample flow cells. The analyzer includes a polarized light source and at least two large angle scattered light photodetectors positioned at acute and right (or oblique) angles to the incident light beams, respectively. Differences in intensities of light measured at the two photodetectors are used to quantify components of the sample U.S. Pat. No. 4,693,602 to Wyatt et al. provides a system for measurement of the scattering properties of very small particles by electro-optical means. The Wyatt '602 system generally requires the use of an intense, though highly spatially inhomogeneous, light source such as a laser. The absolute intensity of the light incident on the particle need not be known. A special structure and measurement process are described by which small particles are differentiated from larger particles grazing the illumination beam.

U.S. Pat. No. 5,530,540 to Wyatt et al. provides a modified light scattering cell, and associated method, whereby an eluant of very small dimension transverse to its direction of flow is entrained successively by two sheath flows and presented to a fine light beam that illuminates the entrained eluant as it flows through the light beam. The light scattered by the entrained eluant is collected by detectors outside of a transparent flow cell enveloping the sheath flow entrained eluant. The windows of the transparent flow cell through which the light beam enters and leaves are far removed from the scattering eluant and kept clear of eluant-contained particles by means of flow components that will form subsequently one of the eluant sheath flows employed. The eluant source is typically from a fine capillary such as found in capillary electrophoresis, capillary hydrodynamic fractionation, and flow cytometry applications.

U.S. Pat. No. 6,651,009 to Trainoff et al. provides a method for measuring the molecular properties of an unfractionated solution of macromolecules. Sharing some similarities with the standard Zimm plot technique, the method begins with the preparation of several sample aliquots spanning a range of concentrations. The aliquots are then injected sequentially into a stream such as provided by a liquid chromatograph. Each aliquot produces an effective "peak" whose elements correspond to different concentrations of the diluted aliquot. By analyzing the angular and concentration dependence of the scattering signals throughout the corresponding peaks, the weight averaged molar mass, the mean square radius, and the second viral coefficient may be derived.

U.S. Pat. No. 6,411,383 to Wyatt provides a method for determining the $2^{nd}$ viral coefficient of an ensemble of molecules dissolved in a selected solvent. Two distinct classes are described: monodisperse and polydisperse molecules. If the molecules are monodisperse, the Wyatt '383 patent teaches that they must be prepared for a chromatographic separation and suitable columns selected. Following standard chromatographic separation procedures, such as exemplified by the method of size exclusion chromatography, the sample passes through the separation columns, a multi-angle light scattering detector, and a concentration detector. The effect of the columns is to produce a concentration profile of the sample that appears as a peak as it passes through the light scattering and concentration detectors. For each elution interval, $v_i$, a corresponding concentration value $c_i$ and set of excess Rayleigh ratios $R_i(\Theta_j)$ is measured for each scattering angle $\Theta_j$. The excess Rayleigh ratios are extrapolated to $\Theta=0°$ resulting in the calculation of a single extrapolated value for each elution slice, viz., $R_i(0°)$. Three sums are calculated from the data collected: 1) the sum of all $c_i$ values over the measured concentration peak; 2) the sum of all $(c_i)^2$ values over the same concentration peak; and 3) the sum of all the extrapolated Rayleigh ratios over the measured light scattering peak. According to the Wyatt '383 patent, the $2^{nd}$ viral coefficient is calculated directly from these three quantities once the molecule's molar mass is known. The same procedure is followed for polydisperse samples; however, the column set is replaced by a dilution means that does not fractionate the sample.

U.S. Pat. No. 5,676,830 to Janik et al. discloses a modified capillary tube used to transfer a liquid sample into a detection cell following separation by a chromatographic system. The capillary tube is modified by plugging or otherwise severely restricting its flow. Near its plugged end, the tube is drilled to provide a plurality of holes or ports perpendicular thereto and penetrating into the central flowing core of the tube so as to direct outflow from the tube perpendicularly therefrom. The outer diameter of this modified capillary tube is selected to be of a size comparable to, though smaller than, the detection cell diameter into which it transfers the flowing sample. In this manner, fluid transferred into a detection cell by the modified capillary tube will be split into a plurality of smaller streams flowing outwardly therefrom and striking the adjacent detector cell walls almost immediately. Because of the close proximity of the emerging split streams to the walls of the detection cell, the eddies produced thereby will be very small and the contents of the detection cell will be homogenized rapidly.

U.S. Pat. No. 4,616,927 to Phillips et al. provides a sample cell that permits measurement of the light scattering properties of very small liquid-borne samples with negligible background interference from the illumination source. The cell construction permits the measurement of illumination intensity at the scattering sample itself, thereby permitting normalization of each detected scattered signal. The cell structure and detection method incorporated therein also permit measurement of extremely small angle-scattered intensities without interference of the incident light beam itself.

U.S. Pat. Nos. 5,250,186 and 5,269,937 to Dollinger et al. describe a high angle light scattering detector using classical Rayleigh scattering. A high intensity arc light source, filtered to leave only one wavelength, illuminates a flow cell. Through the flow cell, very small particles (such as biological proteins) flow in solution after separation by HPLC or some other means. A UV detector generates data regarding the weight concentration of the eluting particles and a scattered light detector collecting scattered light at angles of approximately 90° generates a scattered light signal. The incident light intensity is also measured. The average molecular weight is then computed using the scattered and incident light data, the weight concentration data and a simplified mathematical relationship from which the size factor P and the viral coefficients have been eliminated.

Despite efforts to date, a need remains for advantageous systems and methods for measuring properties of biomolecules, e.g., proteins. In addition, a need remains for systems and methods that permit simultaneous measurement of light scattered intensities and concentration, e.g., using a single flow cell. Moreover, there is a continuing need for systems and methods that permit accurate measurements to be made that support and/or facilitate calculation of the thermodynamic second viral coefficient of molecules, while simultaneously addressing issues associated with IDV and/or band-broadening. These and other needs are satisfied by the apparatus, systems and methods disclosed herein.

SUMMARY OF THE DISCLOSURE

Advantageous apparatus, systems and methods for obtaining desired measurements are provided according to the present disclosure. The disclosed apparatus, systems and methods facilitate measurements of properties associated with biomolecules, e.g., proteins, and in exemplary embodiments, permit simultaneous measurement of scattered light intensities and concentration, e.g., using a single flow cell. Moreover, the disclosed apparatus, systems and methods permit accurate measurements to be made that support and/or facilitate calculation of the thermodynamic second viral coefficient of molecules, while simultaneously addressing issues associated with interdetector delay volume (IDV) and/or band-broadening. Exemplary embodiments of the present disclosure facilitate protein-related measurements using an advantageous dual-detector cell, and the dual-detector cell may be employed in the determination of the second viral coefficient of proteins in aqueous solutions.

Thus, exemplary embodiments of the present disclosure provide advantageous apparatus, systems and methods for simultaneously measuring scattered light intensity at 90° and protein concentration through UV detection as a sample elutes from a size-exclusion chromatography (SEC) column. Exemplary apparatus and systems include a cell usable in flow-mode. The disclosed cell generally includes a main cell casing that defines an interior volume, and multiple ports formed in the main cell casing. The disclosed ports are generally associated with additional system components, including for example: (1) a laser source for light scattering, (2) a 90° light scattering detector, (3) a 15° light scattering detector, (4) a UV source, (5) a UV detector, (6) a sample inlet, and/or (7) a sample outlet.

In at least one embodiment of the present apparatus/system, a fiber optic cable is used in conjunction with a deuterium-lamp UV source and a detector configured for detection of transmitted UV light at 280 nm. In exemplary embodiments thereof, the interior volume of the cell has a capacity in the range of 10 μl, a scattering volume in the range of 0.01 μl, and a path length for UV measurements in the range of 3 mm, although alternative capacities, volumes and/or path lengths may be employed without departing from the spirit or scope of the present disclosure.

In use, exemplary embodiments of the disclosed apparatus/system include a dual-detector cell for performing simultaneous flow-mode measurements of scattered light intensity and protein concentration. In accordance with at least one exemplary embodiment of the disclosed method, a flow rate of 1.0 ml/min, an injection volume of the protein sample of 150 μl, and a concentration of 15 mg/ml, is used. Alternative flow rates, injection volumes, and/or concentrations may be employed without departing from the spirit or scope of the present disclosure.

In further exemplary embodiments of the present disclosure, a method/system is provided whereby characterization of protein self-association may be achieved in a rapid fashion. The method/system entails simultaneous measurement of protein concentration and scattered light intensity in flow mode and analysis of such measurements with respect to modeling data derived from a model that includes a nonideality term. The disclosed measurements are typically performed in conjunction with size-exclusion chromatography (SEC) and the model used to generate modeling data generally includes a term representing the first deviation of ideality.

The disclosed apparatus, systems and methods have a variety of applications and implementations, as will be readily apparent from the disclosure provided herein. Thus, for example, the properties of various biomolecules may be measured using the disclosed apparatus, system and/or method. Additional advantageous features and functionalities associated with the present disclosure will be apparent from the detailed description which follows, particularly when read in conjunction with the figures appended hereto.

BRIEF DESCRIPTION OF THE DRAWINGS

For a more complete understanding of the present disclosure, reference is made to the following detailed description of various exemplary embodiments thereof, considered in conjunction with the accompanying drawings, in which.

DETAILED DESCRIPTION OF EXEMPLARY EMBODIMENT(S)

Figure 1A:
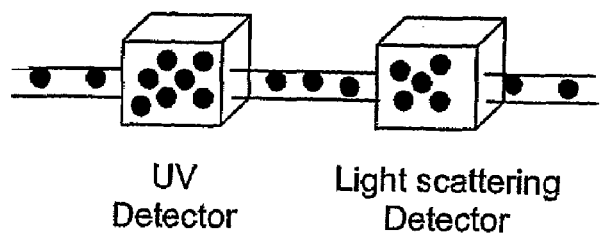
FIG. 1A is a schematic diagram of a prior art measurement system, showing a UV detector and a light scattering detector connected in series in a typical SEC-HPLC setting for molecular weight determination of proteins.

The present disclosure provides advantageous apparatus, systems and methods for obtaining and/or facilitating measurements of properties associated with biomolecules, e.g., proteins. Exemplary embodiments of the present disclosure permit simultaneous measurement of scattered light intensities and concentration. A single flow cell may be employed to simultaneously obtain the desired measurement values, thereby facilitating accurate measurements to be made that support and/or facilitate calculation of the second viral coefficient of molecules (which results from molecule-to-molecule interactions), while simultaneously addressing issues associated with interdetector delay volume (IDV) and/or band-broadening. Exemplary embodiments of the present disclosure facilitate protein-related measurements using an advantageous dual-detector cell, and the dual-detector cell may be employed in the determination of the second viral coefficient of proteins ($B_{22}$) in aqueous solutions.

Measurement of the second viral coefficient ($B_{22}$) according to the present disclosure under given solution conditions generally provides valuable information about the biomolecule of interest. Thus, for example, $B_{22}$ measurements may be employed to derive valuable information concerning biomolecule solubility and/or stability under such solution conditions, e.g., a drug and/or protein solubility/stability. Indeed, the disclosed apparatus, systems and methods may be employed to determine whether a biomolecule in solution, e.g., a protein in solution, exists as a monomer (i.e., a single species), a reversible aggregate (e.g., in self-association), or as an irreversible aggregate.

According to exemplary embodiments of the present disclosure, the advantageous dual-detector cell described herein may be employed with a high-pressure chromatography system to separate impurities or simple syringe pumps to introduce sample(s) for analysis. When two separate syringes are employed to introduce samples, the disclosed apparatus, systems and method may be advantageously employed to determine protein-protein binding constants. Thus, the disclosed apparatus, systems and methods are susceptible to various advantageous implementations and applications, as will be readily apparent to persons skilled in the art from the detailed description provided herein.

By way of background, $B_{22}$ values were extracted from the light scattering and ultraviolet (concentration) chromatograms as generated by the two detectors in a typical SEC setting. The interdetector values, calculated from the peak-to-peak time difference between the two detectors, were observed to vary for protein solutions as a function of solution pH, concentration of protein injected, and volume of protein injected. This variation demonstrated that the IDV calculated under a given solution condition would not be valid for another solution condition. Similar observations are set forth in the literature (Netopilik, 2003; Zammit et al., 1998). It should be noted that this variation in interdetector volume does not affect the calculation of the average molecular weight of the whole peak; however, it does affect the molecular weight calculation when a specific part of the chromatogram is used for the analysis (see FIG. 2 and related description provided herein).

Figure 1B:
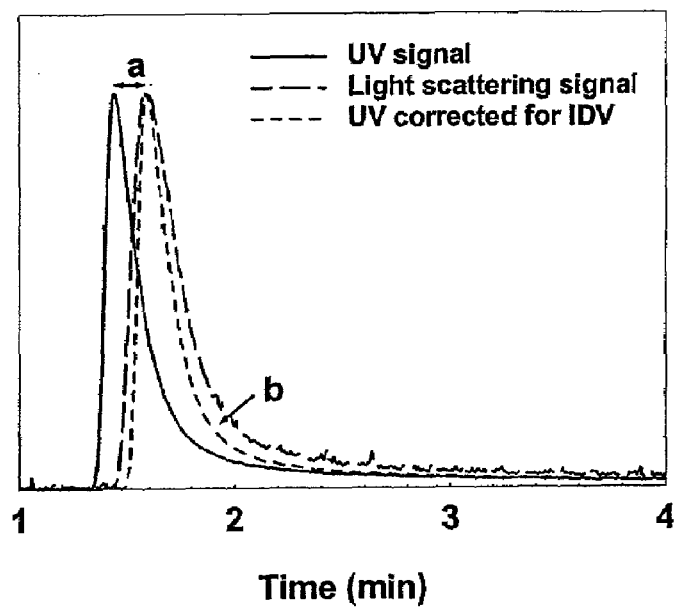
FIG. 1B is a plot illustrating the interdetector volume (IDV) and interdetector band-broadening effects associated with the prior art measurement system of FIG. 1A, the plot reflecting a sample of γ-immunoglobulin injected through an SEC guard column.

Referring now to FIG. 1A, a schematic is provided showing two detectors (UV detector and light scattering detector) connected in series in a conventional, prior art SEC-HPLC setting for molecular weight determination of proteins using laser light scattering. A plot is provided in FIG. 1B indicating the appearance of interdetector delay (Plot a) and interdetector band broadening (Plot b) as the sample passes from one detector to the next connected in series, as demonstrated using a sample of γ-immunoglobulin injected through an SEC guard column. Accordingly, the band broadening effect is seen even after correction for the interdetector volume (IDV).

For analysis of the $B_{22}$ values for control/comparative purposes, specific data points on the chromatogram were utilized, such data points representing different concentrations and scattering intensities rather than the entire chromatogram. Since the molecular weight calculations for a specific part of the chromatogram are affected by variation in IDV value, it is to be expected that the $B_{22}$ values would also be affected. In fact, due to this variation in IDV under different solution conditions, initial attempts to determine the $B_{22}$ values from the SEC utilizing the scattering and the concentration detector were not successful and erroneous values were obtained. The error in IDV resulted in an error in measuring the light scattering intensity for a corresponding concentration for a single data point on the chromatogram. The attempt to determine the values of proteins using two detectors connected in series was further hampered by the issue of interdetector band broadening, which occurs from dilution of the protein sample as it passes from one detector cell to the next detector connected in series (FIG. 1A). It should be noted that, although the IDV can still be determined for a specific solution condition, the issue of band broadening is difficult to correct, since the dilution effect within the detectors is not evenly spread throughout the chromatogram.

Figure 2:
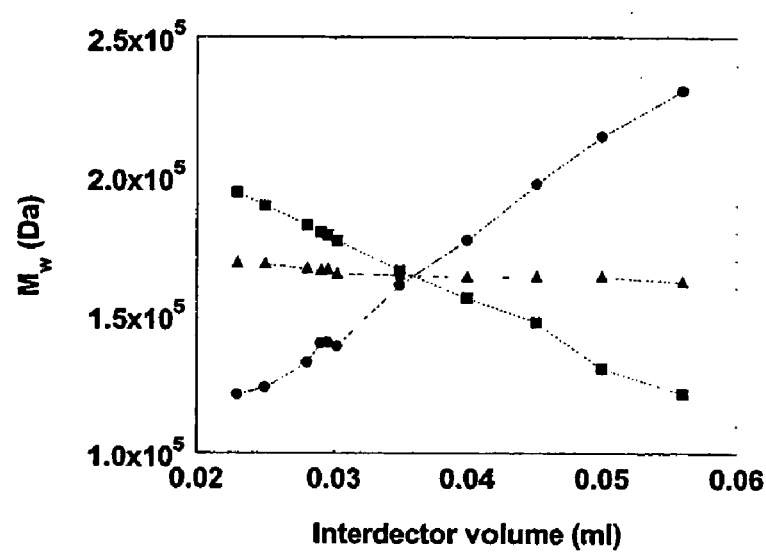
FIG. 2 is a plot illustrating the effect of varying interdetector volumes (IDV) on the calculation of weight-average molecular weight of a monomeric peak of the antibody γ-immunoglobulin (pH 7.4, 150 mM solution ionic strength) using the whole chromatogram, the initial half of the chromatogram, and the latter half of the chromatogram.

Turning now to FIG. 2, the effect of varying interdetector volumes (IDV) on the calculation of weight-average molecular weight of a monomeric peak of the antibody γ-immunoglobulin (pH 7.4, 150 mM solution ionic strength) using the whole chromatogram (▲), the initial half of the chromatogram (●), and the latter half of the chromatogram (■), is illustrated. The lines connecting the data points are provided for viewing convenience. The chromatograms were generated in an SEC-HPLC setting using an LDC/Milton Roy UV detector (Ivyland, Pa.) and a PD-2000 system (Precision Detectors, Inc.; Bellingham, Mass.) hosting a 90° scattering detector. The data were analyzed using Precision/Analyze software (Precision Detectors, Inc.) for calculation of the molecular weight. The software allows calculation of the molecular weight of the whole peak as well as for any specific part of the chromatogram. The IDV was first estimated from the peak/peak difference in the chromatograms from the two detectors (0.035 ml) and then varied manually by adjustments to the software parameters at this approximate IDV value to study the effect of change in IDV on the calculation of molecular weight.

With this background/context and in accordance with the present disclosure, exemplary apparatus, systems and methods for measuring light scattering intensity and concentration simultaneously in flow-mode using size exclusion chromatography (SEC) are provided. In exemplary protein-based applications, the disclosed apparatus, systems and methods provide a reliable and simple means for determining $B_{22}$ values of protein in aqueous solutions. The simultaneous measurement of scattered light intensity and protein concentration is achieved by employing a dual-detector cell in accordance with the present disclosure that is equipped both with a 90° light scattering detector and an ultraviolet (UV) detector.

Such dual-detector cell may be advantageously employed online in a size-exclusion chromatography/high-performance chromatography (SEC-HPLC) setting, and may be designed, constructed and/or employed so as to substantially reduce and/or eliminate the issues of interdetector band broadening and delay volume (see Methods, below, for details). Thus, a range of protein concentrations and their corresponding scattering intensities can be obtained from the eluting protein peak after a single protein injection using the disclosed dual-detector cell to determine the $B_{22}$ values from the resulting Debye plot. This method provides reliable estimates of the $B_{22}$ values of such exemplary proteins as lysozyme, chymotrypsinogen, and chymotrypsin. Indeed, the $B_{22}$ values generated according to the present disclosure correlate closely with $B_{22}$ values obtained using other techniques reported in the related literature.

To further illustrate the design and operation of the disclosed apparatus, systems and methods, and to further elucidate applications, implementations and advantages associated therewith, experimental studies associated with exemplary embodiments of the present disclosure are described hereinbelow. However, it is to be noted that the present disclosure is not limited to or limited by the experimental studies described herein, which are merely illustrative of applications and/or implementations of the disclosed apparatus, systems and methods.

1. Exemplary Experimental Studies
   a. Materials

All buffer components and chemical reagents used in the present studies were of highest-purity grade, obtained from commercial sources, and used without further purification. Chicken egg-white lysozyme (3× crystallized and lyophilized), bovine pancreatic α-chymotrypsinogen A (6× crystallized), α-chymotrypsin from bovine pancreas (3× crystallized from 4× crystallized chymotrypsinogen A), and bovine serum albumin (BSA) were obtained from Sigma-Aldrich Corporation (St. Louis, Mo.) and stored at −20° C. Double-distilled water filtered through a 0.1 µm polycarbonate membrane filter was used for preparation of the mobile phase and protein solutions. For studies with BSA, a 25-mM phosphate buffer (buffer ionic strength=40 mM) was used at pH 7.4. For studies with lysozyme, a 25-mM acetate buffer (buffer ionic strength=16 mM) at pH 4.6 was used. For studies with α-chymotrypsinogen A and chymotrypsin A, a 10-mM citrate buffer was used at pH values 3.0, 5.0, and 6.8. The ionic strength of all solutions was adjusted with NaCl. The final pH of all solutions was measured using a Piccoloplus Hi-1295 digital pH meter (Fisher Scientific, Pittsburgh, Pa.) and adjusted to the desired pH using either 1.0 N NaOH or 1.0 N HCl. All experiments were performed at 25° C.

b. Methods
   i. Size-exclusion chromatography

The chromatograms for the determination of $B_{22}$ were obtained using SEC in an HPLC setting using a Precision Detectors' PD 2000 (Northampton, Mass.) detection system that hosts a 90° light scattering detector followed by a Waters 410 differential refractometer (Waters Corporation, Milford, Mass.). This type of system is routinely used for molecular weight characterization of macromolecules in an SEC setting (Jackson, et al., 1989) and has the advantage that it does not require calibration of the column (Wyatt, 1993a) using various molecular weight markers. In fact, after a single calibration (as described below) using a protein of a well-defined molecular weight, for example bovine serum albumin (BSA), determination of the molecular weight of any given protein can be determined independent of the type of column used and the amount of protein injected as long as the refractive index increment (dn/dc) of the protein is known (Wyatt, 1993a). The details of this method, used for measurement of protein molecular weight, are discussed elsewhere (Wen et al., 1996), the contents of which are hereby incorporated by reference.

In studies associated with the present disclosure, a PD 2000 system was employed for determination of the $B_{22}$ values, since it has the ability to monitor intensity of the scattered light using a 90° light scattering detector as the sample elutes from the SEC column. Importantly, a significant modification was made to the cell that hosts the 90° light scattering detector in the PD 2000 system. More particularly, the cell was modified to incorporate a UV source and a related detector oriented at 180° relative to the UV source. In this way, the intensity of the transmitted UV light was simultaneously monitored, and hence the concentration of the eluting sample was measured as it passed through the cell. At the same time, however, the system behaved similarly to systems configured to perform the conventional light scattering technique for measurement of the $B_{22}$ values, at least one important difference being that the sample is in flow-mode in accordance with the present disclosure, rather than in the conventional batch-mode. A bandpass filter of 280 nm was used at the detector port to allow measurement of protein absorbance.

Figure 3A:
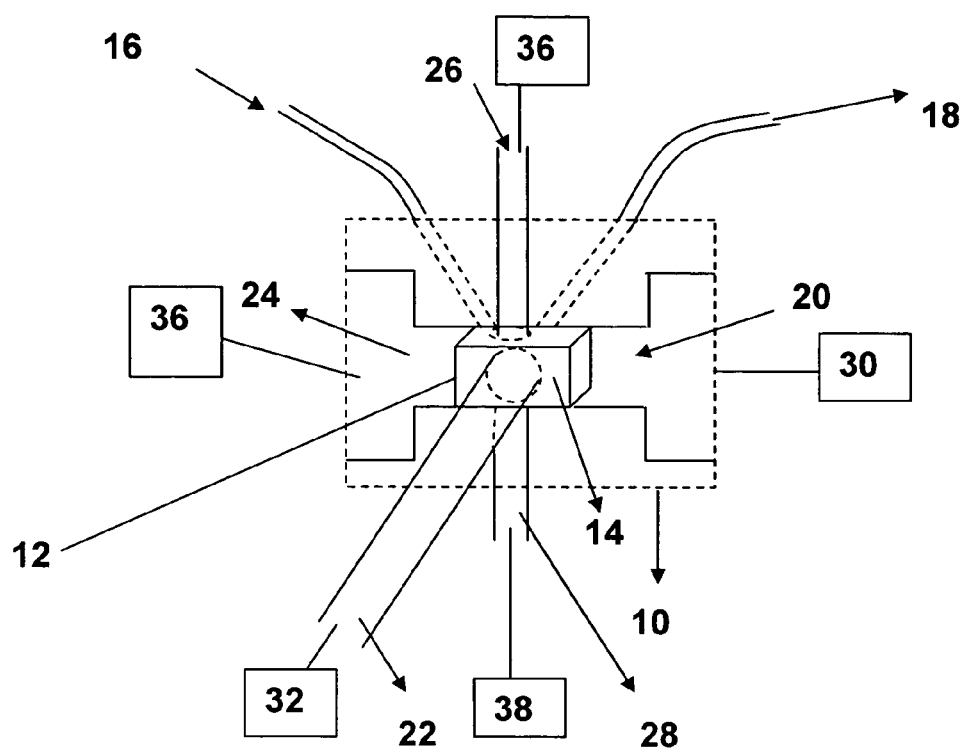
FIG. 3A is a perspective front view, rendered at least partially schematically, of a light scattering and detection apparatus/system including a flow through-type sample cell in accordance with an exemplary embodiment of the present disclosure that permits simultaneous measurements of scattered light intensity and protein concentration.
Figure 3B:
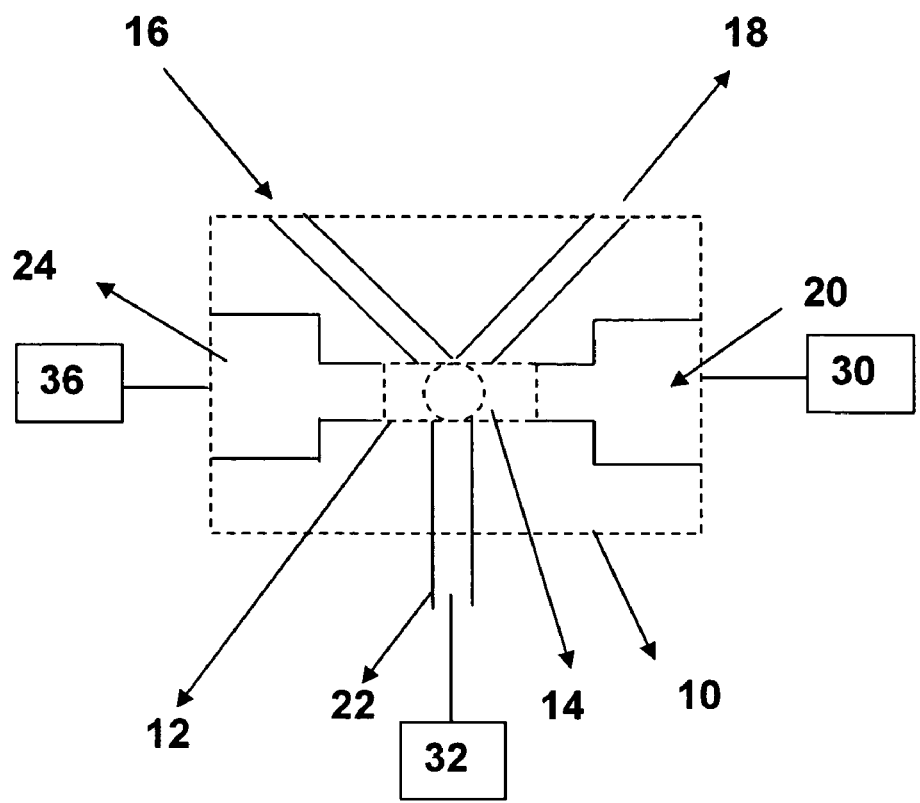
FIG. 3B is a top view of the exemplary light scattering and detection apparatus/system of FIG. 3A.

Shown at least partially schematically in FIGS. 3A and 3B is an apparatus 10 for light scattering and detection in accordance with an exemplary embodiment of the present disclosure. The disclosed apparatus 10 permits simultaneous measurements of scattered light intensity and concentration in flow-through mode. Exemplary apparatus 10 includes a sample cell 12 defining an interior volume 14, a first side occupied by a sample inlet 16, and a second side occupied by a sample outlet 18. The sample cell 12 may be termed a "flow-through" cell that is configured to receive a continuous flow of protein solution from a SEM column (not shown) at its first side via the sample inlet 16 and to continually discharge such flow at its second side via the sample outlet 18.

Ports 20, 22, 24, 26, and 28, shown schematically in FIGS. 3A and 3B, occupy respective third, fourth, fifth, sixth, and seventh sides of the cell 12 for permitting light and/or light beams to pass into the interior volume 14 of the cell 12, into and through a solution passing through the cell 12 (e.g., a protein solution), and/or outward of the interior volume 14 of the cell 12 for measurement of scattered light and/or concentration (e.g., protein concentration). A laser light source 30 is interoperably coupled to the cell 12 via the port 20 for directing a laser light beam (not shown) into the cell 12, a detector 32 is interoperably coupled to the cell 12 via the port 22 for receiving and detecting 90° scattered light from the laser light beam emerging from the cell 12, and a detector 34 is interoperably connected to the cell 12 via the port 24 for receiving and detecting 15° scattered light from the laser light beam emerging from the cell 12.

An ultraviolet (UV) light source 36 is interoperably connected to the cell 12 via the port 26 for directing a UV light beam into the cell 12, and a detector 38 is interoperably connected to the cell 12 via the port 28 for receiving and detecting unscattered UV light from the UV light beam emerging from the cell 12. Ports 26 and 28 are aligned with each other and oriented at approximately a 90° angle to the laser light beam (not shown) directed by the laser light source 30 into the cell 12 so as to minimize the potential for interference between and among the detectors 32, 34, 38. The laser and UV light sources 30, 36 and the detectors 32, 34, 38 are all shown schematically for the sake of convenience and simplicity.

In exemplary experimentation according to the present disclosure, a laser light source 30 was employed that produced collimated light at a wavelength of 685 nm. In addition, a fiber-optic cable type UV light source hosting a deuterium lamp and manufactured by MiniDATA UV (Analytical Instrument Systems, Flemington, N.J.), and a detector 38 for detection of transmitted UV light at 280 nm, were employed. The cell volume in the experimental system was 10 μl and the scattering volume was 0.01 μl. The path length for UV measurements was 3 mm.

For SEC, a Spectra Physics P4000 pump (Spectra Physics, Mountain View, Calif.) in conjunction with a Rheodyne 7725 manual injector (Rheodyne, Rohnert Park, Calif.) with a 200 μl injection loop was used in the experimental system described herein. A flow rate of 1.0 ml/min and an injection volume of 150 μl of the protein sample, with a concentration of 15 mg/ml, were used for all studies, unless otherwise specified. For each protein-buffer system, the samples were injected in triplicate. For studies with BSA, a TSK-G3000SWXL column (250 Å pore size, 5 μm bead size, and 30 cm×0.8 cm column dimensions) from Tosoh Bioscience (Montgomeryville, Pa.) was used. For studies with lysozyme, a YMC-pack Diol-60, DL06S05-3008WT column (60 Å pore size, 5 μm bead size, and 30 cm×0.8 cm column dimensions) from YMC (Kyoto, Japan) was used. For studies with α-chymotrypsinogen A and α-chymotrypsin A, a TSK-G2000SWXL (125 Å pore size, 5 μm bead size, and 30 cm×0.8 cm column dimensions) from Tosoh Bioscience was used. Appropriate guard columns were employed before the main columns.

While a high-pressure chromatography apparatus is described herein as having been used for experimentation, the disclosed apparatus, system and method are not limited thereto, but can be used with syringe pumps to introduce a protein sample for analysis. When two separate syringes are used to introduce the samples, the apparatus, system and method of the present disclosure can be used to determine protein-protein binding constraints.

c. Data Analysis

In the common/conventional approach, the viral coefficient of proteins in aqueous solutions using the technique of static light scattering is obtained by construction of the Debye plot (Tanford, 1961). The Debye equation is written as $$\frac{Kc}{R_\theta} = \frac{1}{M} + 2B_{22}c, \quad (1)$$

where $R_\theta$ is the excess Rayleigh's ratio of the protein in solution of concentration c, and M is the weight average molecular weight of the protein, K is the optical constant and is defined as $$K = \frac{4\pi^2 n^2 (dn/dc)^2}{N_A \lambda_o^4}, \quad (2)$$

where n is the solvent refractive index, dn/dc is the refractive index increment, λ is the wavelength of the incident light, and $N_A$ is the Avogadro's number. Experimentally, a Debye plot is constructed by preparing several solutions of varying protein concentrations and measuring the respective Rayleigh's ratios. The viral coefficient is then determined from the slope of the plot of $KC/R_\theta$ versus c.

In accordance with the present disclosure, the Debye plot is advantageously generated from a single injection of a biomolecular solution, e.g., a protein solution. The chromatograms that are simultaneously obtained from the UV detector and the light scattering detector are analyzed to generate the Debye plot. These measurements may then be employed to obtain the $B_{22}$ value of the given biomolecule/protein under a given solution condition. The range of protein concentrations and the corresponding scattered light intensities are obtained from various chromatogram points. Since the chromatogram appears as a band, a range of protein concentrations can be obtained, with the highest at the peak and lowest near the baseline of the chromatogram. Each point on the chromatogram represents a collection interval, the upper limit of which is decided by the duration of the collection of the chromatogram. In accordance with the experimental studies described herein, the collection time was varied from 0.5 s to 1.5 s. The duration of sample collection did not affect the results presented herein. Each data point on the chromatogram represented an average of the scattered light intensity (and the transmitted UV intensity) from the sample volume that passed through the interior volume 14 of the cell 12 in this data collection time. The scattered light intensity at 90° and the intensity of the transmitted UV light at 280 nm were/are converted to $R_\theta$ and concentration, respectively, as described below.

Molecular weight of the protein sample in dilute solutions and for polarized light is related to intensity of the scattered light from the sample through the equation $$Mw = \frac{N_A \lambda_o^4 R^2 I_s}{4\pi^2 \sin^2 \phi c \left(\frac{dn}{dc}\right)^2 n^2 I_o}, \quad (3)$$

where $N_A$ is the Avogadro's number, X is the wavelength of the incident radiation, R is the distance of the sample from the detector, $I_s$ is the intensity of the scattered light, $I_o$ is the intensity of the incident light, c is the concentration of protein sample, dn/dc is the refractive index increment of protein solution, φ is the angle between the plane of the incident polarized light and the scattering detector, and n is the refractive index of the solvent. Upon collecting all the constants and instrument parameters into an overall light scattering instrument constant $A_{90}$, Eq. 3 can be written as $$Mw = \frac{I_s}{A_{90} c \left(\frac{dn}{dc}\right)^2}, \quad (4)$$

where $$A_{90} = \frac{I_o 4\pi^2 n^2}{N_A \lambda_o^4 R^2}. \quad (5)$$

Since the intensity of the incident radiation, Io, and the distance between the sample detector, R, is fixed, the ratio of these two parameters can be obtained by rearranging the above equation, and is represented as $K_1$, i.e., $$\frac{R^2}{I_o} = \frac{4\pi^2 n^2}{N_A \lambda_o^4 A_{90}} = K_1. \quad (6)$$

Hence $K_1$ can be simply obtained from the instrument constant $A_{90}$, the wavelength of the incident light (685 nm), and the refractive index of the solution. Rayleigh's ratio at 90° scattering angle is defined as $$R_\theta = \frac{I_s R^2}{I_o}. \tag{7}$$

Combining Eqs. 6 and 7, Rayleigh's ratio can now be expressed as $$R_\theta = K_1 I_s. \tag{8}$$

Eq. 8 provides a simple means of obtaining Rayleigh's ratio of a given data point on the light scattering chromatogram, once the instrument has been calibrated using an appropriate standard.

The concentration for each corresponding data point on the UV chromatogram was estimated from the UV signal intensity. In the exemplary instrument configuration described herein, the UV chromatogram represented the intensity of the transmitted light. Hence the concentration of the injected protein at each data point was estimated using the equation $$c_{(g/ml)} = \log\left(\frac{I_{100\%\,T} - I_{0\%\,T}}{I_a - I_{0\%\,T}}\right) \cdot 10/(E_{1\%}b), \tag{9}$$

where c is the concentration of the protein, $I_{100\%T}$ is the intensity of the UV signal at the baseline, $I_{0\%T}$ is the signal of the UV detector in off-mode, $I_a$ is the UV signal at a given time point on the chromatogram, $E_{1\%}$ is the extinction coefficient of 1% protein solution, and b is the path length of the UV cell (3 mm). The following $E_{1\%}$ values at 280 nm were used for the calculation of concentrations of various proteins studied: lysozyme, 26.4; chymotrypsinogen and chymotrypsin, 20.4; and BSA, 6.67.

Once the $R_\theta$ values and the corresponding concentrations are obtained for data at each time point on the chromatogram, the Debye plot is constructed according to Eq. 1 and the viral coefficient is obtained from the slope of this plot. An important parameter for the construction of the Debye plot is K, which depends on the square of the dn/dc of the protein solution and the refractive index of the solvent. Since the dn/dc of a given protein varies depending on solution conditions and significantly affects the value of K, this value must be determined for each different solution condition. In accordance with the present disclosure, this value is determined directly from the chromatogram obtained for the differential refractive index (DRI) detector after calibration of this detector using a standard of known dn/dc (see the section hereinbelow entitled "Calibration"). This is another advantage of using SEC along with light scattering, UV, and DRI detector, since the dn/dc can be obtained from the same injection that is used for the determination of the $B_{22}$ value. The refractive index of the NaCl solution of a given ionic strength, similar to that of the buffer (mobile phase), was used as the refractive index of the solvent for all calculations.

d. Calibration

The calibration of the equipment according to the experimental studies described herein was carried out to determine the constant $A_{90}$ for determination of $R_\theta$ and the DRI constant, defined as B, to determine the dn/dc of a given protein. For this purpose, BSA was used as the standard. One-hundred microliters of a 2-mg/ml BSA solution at pH 7.4 was injected into a TSK3000SWXL size-exclusion column. A dn/dc of 0.167 and molecular weight of 66,000 was used to calculate calibration constants from the monomer peak of BSA. Under these conditions, the following calibration constants were obtained using the Precision/Analyze software (Precision Detectors): $K_{90}=(B/A_{90})=4569.8$ and B=54618.1. $A_{90}$ is then obtained by dividing B with $K_{90}$. Once the DRI constant, B, is obtained, the dn/dc of any given protein for a given solution condition can be determined as long as the molecular weight of the protein is known. The dn/dc value is estimated by varying its value in the calculation parameters until the calculated molecular weight from this technique is similar to the reported molecular weight.

2. Exemplary Results and Discussion

Figure 4A:
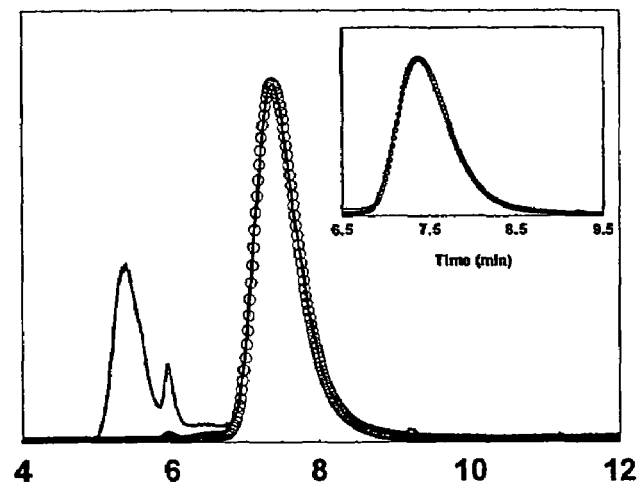
FIG. 4A shows a plot including chromatograms for lysozome eluted through a SEC column at pH 4.6 (NaCl concentration=40 mM) with simultaneous measurements by the 90° light scattering detector and the UV detector associated with the exemplary cell of FIGS. 3A and 3B, and an expanded view (inset) of the latter half of the monomeric lysozome chromatogram indicating several data points generated by the UV and light scattering detectors.
Figure 4B:
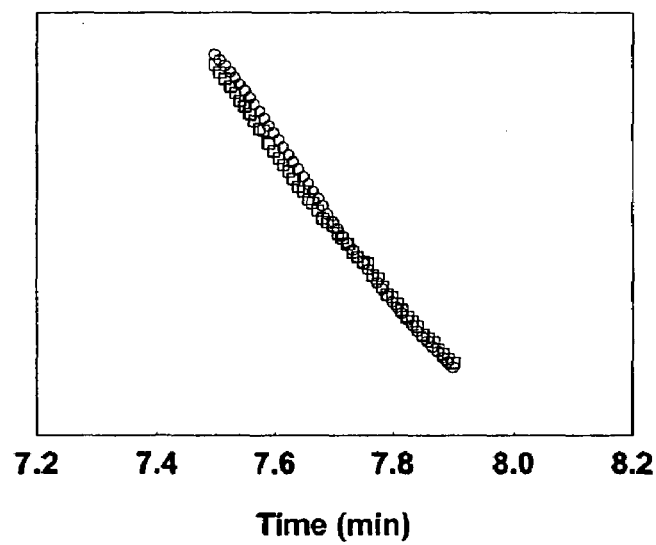
FIG. 4B shows an expanded view of the latter half of the monomeric species of lysozyme.

Referring now to FIGS. 4A and 4B, the plot provided in FIG. 4A represents chromatograms for lysozyme eluted through a SEC column at pH 4.6 (NaCl concentration=40 mM) generated with simultaneous detection by the 90° light scattering detector 32 (solid line) and the UV detector 38 (○) in accordance with an exemplary embodiment of the present disclosure. FIG. 4B shows an expanded view of the latter half of the monomeric species of lysozyme indicating absence of interdetector delay volume or band broadening. This expanded view further indicates several data points generated by the respective UV (○) and light scattering (□) detectors 38, 32.

As discussed hereinabove, exemplary apparatus 10 and/or the multiport, dual-detector cell 12 associated therewith is designed and constructed so as to permit, when used (for example) in flow mode and in conjunction with SEC, simultaneous measurement of protein concentration and scattered light intensity at 90°, and to thereby provide a means to estimate $B_{22}$ of proteins in aqueous solutions through construction of the Debye plot. The chromatograms of lysozyme shown in FIG. 4A were recorded from signals obtained by light scattering and UV detectors, and reflect normalization of the chromatograms to a value of 1.0 at the peak maximum. The normalization was carried out only to facilitate comparison of the two chromatograms and was not used for the calculations of $B_{22}$. As is evident from the expanded view of the lysozyme monomer in FIG. 4B, the light scattering and the UV chromatograms more or less completely overlay each other and show no interdetector band broadening or delay volume, especially as compared to prior art systems wherein detectors are connected in series. Hence, at each time point, the scattered light intensity of the protein sample on the light scattering chromatogram corresponds to its exact concentration at that point on the UV chromatogram. Furthermore, the higher molecular weight species or aggregates are well separated from the monomeric peak of lysozyme. This is important since in batch-mode static light scattering studies such a separation is not attainable-resulting in an error in the measurement of the true scattered intensities.

It is also evident from FIG. 4A that several data points are present on either side of the peak of the chromatograms, each of which represents a protein concentration and its corresponding scattered light intensity. In principle, one can use either side of the chromatogram to obtain a range of concentrations. In the experimental studies described herein, the latter half of the peak was selected for analysis, as it generated more reproducible results. The enhanced reproducibility may be attributable to the fact that the initial half of the peak is somewhat affected by the aggregate peak in the light scattering chromatogram (the baselines do not completely overlap at the beginning of the chromatogram). The expanded view of the latter half of the normalized chromatograms shown in FIG. 4B illustrates that a range of several concentrations and their corresponding scattering intensities can be obtained from a single injection of the protein.

Figure 5A:
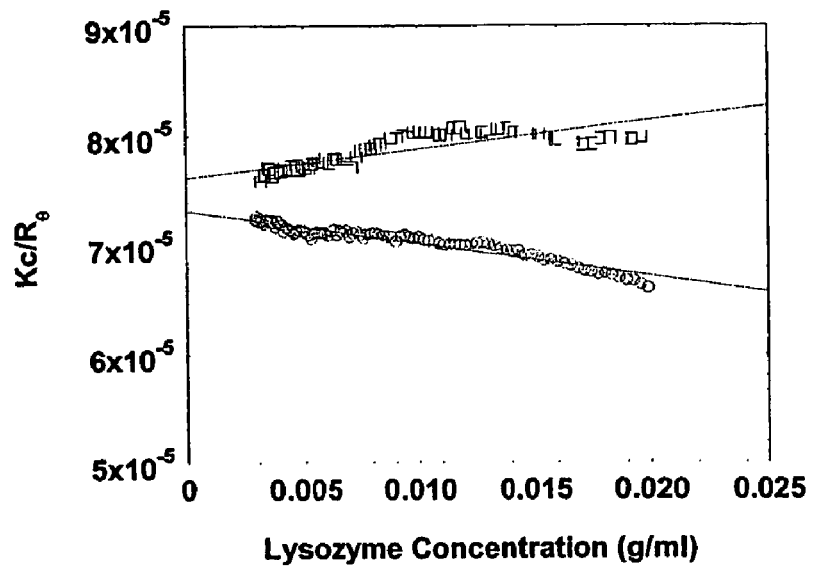
FIG. 5A showsDebye plots of lysozome at pH 4.6 and NaCl concentrations of 40 mM and 400 mM.
Figure 5B:
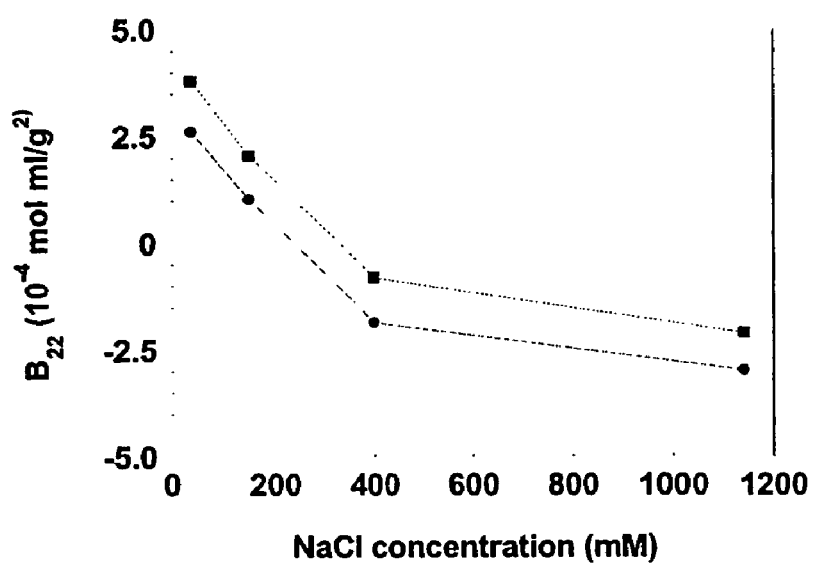
FIG. 5B shows plots of $B_{22}$ values of lysozome at pH 4.6 and varying NaCl concentrations determined by the presently disclosed apparatus/system and method as compared to reported literature for batch-mode static light scattering method.

Referring now to FIGS. 5A and 5B, Debye plots (Kc/R$_\theta$ versus c) of lysozyme at pH 4.6 and NaCl concentrations of 40 mM (□) and 400 mM (○) are provided in FIG. 5A. The lines are generated by linear regression of the data points and the slope of the line represents the B$_{22}$ of lysozyme under these solution conditions. FIG. 5B illustrates B$_{22}$ values of lysozyme at pH 4.6 at varying NaCl concentrations determined by the exemplary methods described herein (●) in comparison to the values of same (■) which are reported in the relevant literature as having been obtained by the batch-mode static light scattering method (Rosenbaum and Zukoski, 1996).

For the determination of B$_{22}$, each individual data point on the UV chromatogram and the corresponding data point on the light scattering chromatogram are converted to concentration and Rayleigh's ratio, respectively, as described hereinabove in the section entitled "Data Analysis". After calculating the value of K (defined in Eq. 2), a plot of Kc/R$_\theta$ versus c is then generated for all these points, resulting in the plot depicted in FIG. 5A, from which several features are evident. As demonstrated herein, the disclosed apparatus, systems and methods provide an advantageous way of generating the Debye plot and hence estimating B$_{22}$ values which closely correlate to the values obtained from a batch-mode static light scattering method. Furthermore, a range of concentrations (e.g., ~5-20 mg/ml) with several intermediate concentrations can be obtained from a single injection, e.g., an injection of 150 μl of a 30-mg/ml lysozyme solution, thus providing enough data for a reliable linear regression analysis. Most importantly, the disclosed apparatus, systems and methods can be used to estimate and track positive and negative B$_{22}$ values, e.g., B$_{22}$ values of lysozyme at pH 4.6 for various solution ionic strengths which are similar to those reported in literature under the given solution conditions (see, e.g., FIG. 5B). Clearly, the values obtained according to the disclosed apparatus, systems and methods agree well quantitatively with those previously reported in the literature.

Figure 6A:
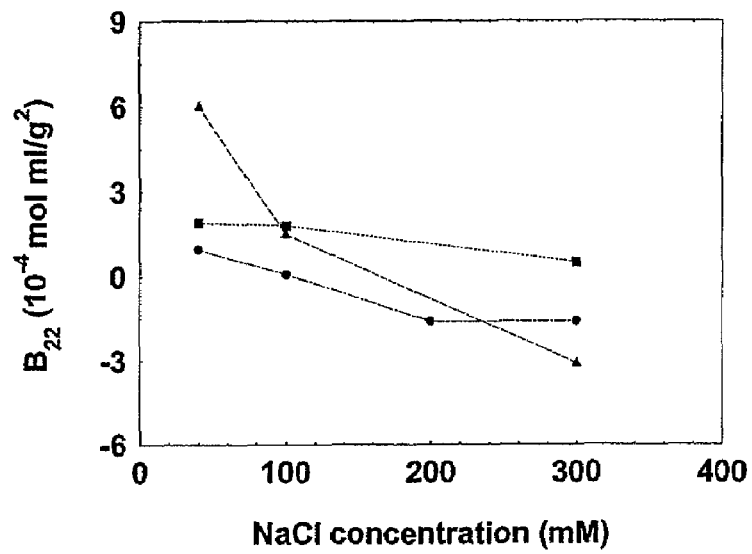
FIGS. 6A and 6B show $B_{22}$ values determined by the presently disclosed apparatus/system and method, of chymotrypsinogen at pH 3.0 and at varying NaCl concentrations, and of chymotripsinogen at NaCl concentration of 300 mM and at varying pH, as compared to corresponding values therefor reported in literature and obtained either by the batch-mode static light scattering method, or by self-interaction chromatography.
Figure 6B:
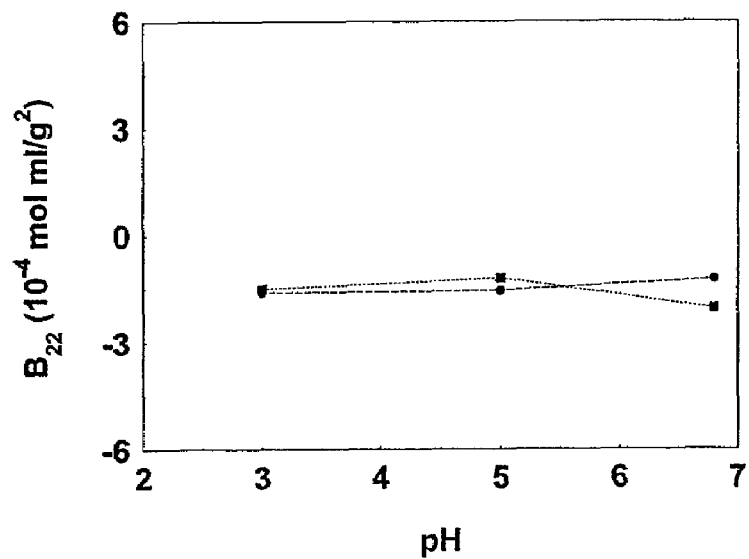

Referring now to FIGS. 6A and 6B, B$_{22}$ values of chymotrypsinogen are shown at pH 3.0 and at varying NaCl concentrations, and chymotrypsinogen at NaCl concentration of 300 mM and at varying pH, determined by the exemplary apparatus, system and method of the present disclosure (●) compared to the values of same which are reported in the relevant literature as having been obtained either by batch-mode static light scattering method (Velev et al., 1998) (▲), or by self-interaction chromatography (Tessier et al., 2002) (■).

To test the validity and generality of the disclosed apparatus, systems and methods of the present disclosure for the measurement of B$_{22}$, further experiments were conducted on α-chymotrypsinogen A, whose B$_{22}$ values have been well reported in literature under various solution conditions. FIG. 6A shows that the B$_{22}$ values obtained by the exemplary apparatus, system and method of the present disclosure follow similar trends compared to those reported in literature for the various solution conditions studied. It should be noted that the absolute values may not match since different techniques may result in different values of B$_{22}$, as has been previously reported in similar types of studies (Bloustine et al., 2003; Teske et al., 2004; Velev et al., 1998). These differences have been attributed either to the effect of systematic errors associated with the techniques or to the multiple-body interaction of solute with each other (e.g., solute in the mobile phase interacting with multiple immobilized solutes in affinity chromatography). Furthermore, it should be noted that batch-mode light scattering incorporates scattering contributions from everything that is present in solution, e.g., aggregates and dust particles, whereas in SEC, such contributions are eliminated. Hence, the net result of these factors could result in a disagreement in the comparison of absolute values of B$_{22}$ among various techniques.

Figure 7:
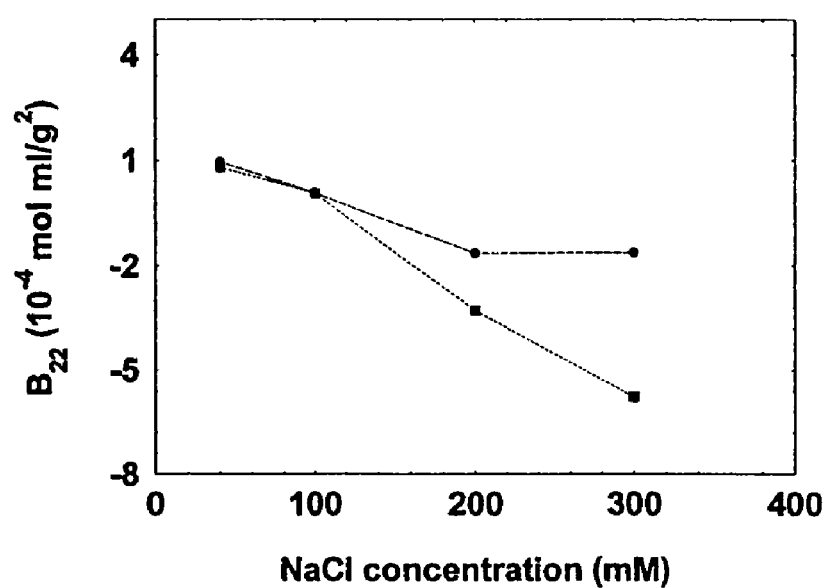
FIG. 7 shows the $B_{22}$ values, determined by the presently disclosed apparatus/system and method, of chymotrypsinogen and chymotrypsin at pH 3.0 at varying NaCl concentrations.

Referring now to FIG. 7, B$_{22}$ values of chymotrypsinogen (●) and chymotrypsin (■), as determined in accordance with the present disclosure at pH 3.0 and at varying NaCl concentrations, are shown. Chymotrypsin is a related protein to chymotrypsinogen and in fact can be obtained from chymotrypsinogen through autocatalytic activation of the latter. Hence, the protein-protein interactions in chymotrypsin are presumed to be similar to those present in chymotrypsinogen, providing yet another way to test the validity of the apparatus, system and method of the present disclosure, since under a given set of solution conditions, similar values of B$_{22}$ should be obtained for each such protein.

FIG. 7 shows that at pH 3.0 for 40-mM and 100-mM solution NaCl concentrations, similar B$_{22}$ values are obtained for these two proteins, but that at 200-mM and 300-mM NaCl concentrations, a significant difference appears therebetween. Evidently, at higher NaCl concentrations, the experimental results presented herein demonstrate that the net protein-protein interactions are not similar for these proteins and appear to be more attractive for chymotrypsin compared to that for chymotrypsinogen. These data demonstrate the applicability of the disclosed apparatus, system and method in identifying different protein-protein interactions, even when the proteins are closely related to each other.

Table 1, presented immediately hereinbelow, shows a summary of the B$_{22}$ values of the various proteins studied under different solution conditions in accordance with this disclosure as compared to the values of same reported in literature as having been obtained using the batch-mode static light scattering technique. The standard deviation in the B$_{22}$ values for all solutions obtained in this study was <0.3×10$^{-4}$ mol ml/g$^2$. These results demonstrate the utility associated with use of the presently disclosed flow-mode static light scattering apparatus, system and method with dual-detectors in a single cell in conjunction with SEC to determine the B$_{22}$ values of proteins in aqueous solutions. The advantages offered thereby include: (1) a smaller amount of protein required (B$_{22}$ values can be obtained from a single protein injection); (2) a minimum contribution of dust; (3) separation of aggregates from monomeric species; and/or (4) amenability to high throughput screening from the use of automated SEC-HPLC systems (which can run several samples in a short duration of time).

TABLE 1

B$_{22}$ values of various proteins under different solution conditions, as determined by the disclosed apparatus, system and method as compared to the values of same reported in literature as having been obtained using the batch-mode static light scattering technique.

| Solution conditions (pH, NaCl concentration) | B$_{22}$, (10$^{-4}$ mol ml/g$^2$) | |
|---|---|---|
| | Experimental Results (mean ± S.D., n = 3) | Literature Values |
| Lysozyme | | |
| pH 4.6, 40 mM | 2.6 ± 0.1 | 3.8* |
| pH 4.6, 150 mM | 1.0 ± 0.2 | 2.0 |

TABLE 1-continued $B_{22}$ values of various proteins under different solution conditions, as determined by the disclosed apparatus, system and method as compared to the values of same reported in literature as having been obtained using the batch-mode static light scattering technique.

| | $B_{22}$, $(10^{-4}$ mol ml/g$^2)$ | |
|---|---|---|
| Solution conditions (pH, NaCl concentration) | Experimental Results (mean ± S.D., n = 3) | Literature Values |
| pH 4.6, 400 mM | −1.8 ± 0.1 | −0.8 |
| pH 4.6, 1.14 M | −3.0 ± 0.3 | −2.1 |
| Chymotrypsinogen | | |
| pH 3.0, 40 mM | 0.9 ± 0.1 | 6.0† |
| | | 1.9‡ |
| pH 3.0, 100 mM | 0.1 ± 0.1 | 1.5 |
| | | 1.8 |
| pH 3.0, 200 mM | −1.6 ± 0.2 | — |
| pH 3.0, 300 mM | −1.6 ± 0.2 | −1.5 |
| | | 0.5 |
| pH 5.0, 300 mM | −1.6 ± 0.2 | −1.2 |
| pH 6.8, 300 mM | −1.2 ± 0.2 | −2.0 |
| Chymotrypsin | | |
| pH 3.0, 40 mM | 0.8 ± 0.1 | — |
| pH 3.0, 100 mM | 0.1 ± 0.01 | — |
| pH 3.0, 200 mM | −3.3 ± 0.3 | — |
| pH 3.0, 300 mM | −5.8 ± 0.3 | — |

*(Rosenbaum and Zukoski 1996)
†(Velev et al., 1998)
‡(Tessier et al., 2002)

3. Rapid Characterization of Protein Association by Size-Exclusion Chromatography Through Simultaneous Measurement of Concentration & Scattered Light Intensity Characterization of protein self-association is an integral part of understanding the behavior and role of proteins in cellular processes at the molecular level. Concurrently, the fast emergence of a proteomics-based biotechnology industry demands that protein association behavior be characterized rapidly, possibly utilizing a high throughput-based method. Recently, additional interest has been generated for studying protein self-association at relatively high concentration, for example, in the presence of crowding agents as sugars and nonionic polymers, to understand the effect of molecular crowding on proteins in cells (Kozer, N. et al., "Effect of crowding on protein-protein association rates: Fundamental differences between low and high mass crowding agents," J. Mol. Biol. 336:763-774, 2004; Patel, C. N. et al., "Effects of molecular crowding by saccharides on a-chymotrypsin dimerization," Protein Sci. 11:997-1003, 2002; and Nichol, L. W. et al., "Effect of inert polymers on protein self-association," FEBS Lett. 126:18-20, 2001.) Similarly, reversible protein self-association is a critical issue in development of high concentration protein solutions for therapeutic use as those of antibodies (Shire, S. J. et al., "Challenges in the development of high protein concentration formulations." J. Pharm. Sci. 93:1390-1402, 2004.) Self-association at high protein concentration could also affect bulk manufacturing processes due to enhanced viscosity and/or reduced solubility (Id.; Hall, C. G. et al., "Reversible self-association of a human myeloma protein. Thermodynamics and relevance to viscosity effects and solubility." Biochemistry. 23:5123-5129, 1984.) Characterization of protein self-association is crucial because often the monomeric and the oligomeric states have different biological properties. Thus, it is essential to know which state is more populated under what conditions. By definition, total protein concentration is the determining factor for a given solution condition that regulates whether the monomeric state or the oligomeric state is more populated. In addition, solution properties such as pH, ionic strength, temperature and/or co solutes, play an important role as these could affect the interactions involved in self-association.

For characterization of protein self-association, one essentially requires a profile of the change in the molecular weight of the protein as a function of protein concentration, without any contribution from the non-ideality term, i.e., the second viral coefficient. Debye plot, essentially, can generate this information since $R_\Theta$ is directly proportional to the molecular weight of the species and is a function of protein concentration as well.

βLg and ChyA have been characterized extensively for their self-association behavior and are routinely used as calibration standards in sedimentation equilibrium studies. βLg exhibits salt-dependent monomer-dimer equilibrium at acidic pH. At low ionic strength and low pH (pH 2.3), βLg exists as pure monomer ($M_w$=18.4 KDa), whereas at high ionic strengths (~1 M) and moderately high pH (pH 3.0), it exists primarily as a dimer. At intermediate solution conditions βLg exhibits various levels of monomer-dimer equilibrium depending on pH and ionic strength. The association constants of βLg self-association under various solution conditions are well reported in literature (Sakurai, K., M. et al., Salt-dependent monomer-dimer equilibrium of bovine b-lactoglobulin at pH 3." Protein Sci. 10:2325-2335, 2001.) Similary, ChyA ($M_w$=25 KDa) has been shown to exhibit salt-dependent monomer-dimer equilibrium at moderately acidic pH (pH 4.0) and the equilibrium association constants have also been reported (Timasheff, S. N. et al, "Dimerization of a-chymotrypsin. II. Ionic strength and temperature dependence." Biochemistry. 10:1617-1622, 2001.)

Based on experimental data obtained for Bovine β-lactoglobulin A and bovine α-chymotrypsin A, it was evident that linear Debye plots are obtained under conditions where βLg exists primarily as a monomer and as a dimer, whereas, curved Debye plots are obtained under conditions where βLg exhibits monomer-dimer association equilibrium. Based on thereon, steps were taken to develop/use a model to analyze curved Debye plots in an attempt to retrieve the association constants for monomer-dimer equilibrium.

Model for Self-Association and Data Analysis.

A monomer-dimer equilibrium is written as $$M + M \overset{K_D}{\rightleftharpoons} D \tag{10}$$

Where the association constant $K_D$ is defined as, $$K_D = \frac{[c_d]}{[c_m]^2} \tag{11}$$

Where $[C_d]$ is the molar concentration of the dimer and $[c_m]$ is the molar concentration of the monomer. The total molar concentration, $[c_t]$, of the protein can be written in terms of the monomer concentration as,

$$[c_t]=[c_m]+2[c_d] \tag{12}$$

Combining Eq. 11 and 12, solving the resulting quadratic equation for positive solution of $[c_m]$ and $[C_d]$ and converting molar concentration to g/ml, the monomer and dimer concentration can be written as, $$c_{monomer} = \frac{-1 + (1 + 8000 Kc_t/M_m)^{\frac{1}{2}}}{4K/M_m} \quad (13)$$

$$c_{dimer} = \frac{1 + 4000 Kc_t/M_m - (1 + 8000 Kc_t/M_m)^{\frac{1}{2}}}{4000 K/M_m} \quad (14)$$

For an associating system, the Debye equation is written as, $$\frac{Kc_t}{R_\theta} = \left(\frac{1}{M_{av}} + Bc_t\right) \quad (15)$$

Where, $M_{av}$ is the weight average molecular weight of all the species present in the solution. It is noted that $B_{22}$ has been substituted with the term B to represent the nonideality arising from monomer-monomer, monomer-dimer and dimer-dimer interactions. Considering that there is negligible contribution of nonideality towards the curvature, a first approximation is to assume the term B to be zero. This assumption is routinely used in the analysis of sedimentation equilibrium data (Timasheff, S. Net al., "Dimerization of a-chymotrypsin. I. pH dependence in the acid region." Biochemistry. 10:1609-1617, 1971.) The Debye equation is then simplified to, $$\frac{Kc}{R_\theta} = \frac{1}{M_{av}} \quad (16)$$

For an associating system, the change in the chemical potential of the solvent with solute concentration is written as, $$\frac{\partial \mu_1}{\partial c_t} = \frac{\partial c_m}{\partial c_t \cdot M_m} + \frac{\partial c_d}{\partial C_t \cdot 2M_m} + \frac{\partial (Bc_t^2)}{\partial c_t} \quad (17)$$

Once again, assuming B=0 in Eq. 17, substituting for $c_m$ and $C_d$ from Eq. 13 and 14, taking partial derivatives and using the result in the derivation of the Rayleigh's light scattering equation, the following Debye equation is obtained, $$\frac{Kc_t}{R_\theta} = \frac{1}{M_{av}} = \frac{(1 + 8K_D c_t/M_m)^{1/2} + 1}{2(1 + 8K_D c_t/M_m)^{1/2} M_m} \quad (18)$$

Figure 8A:
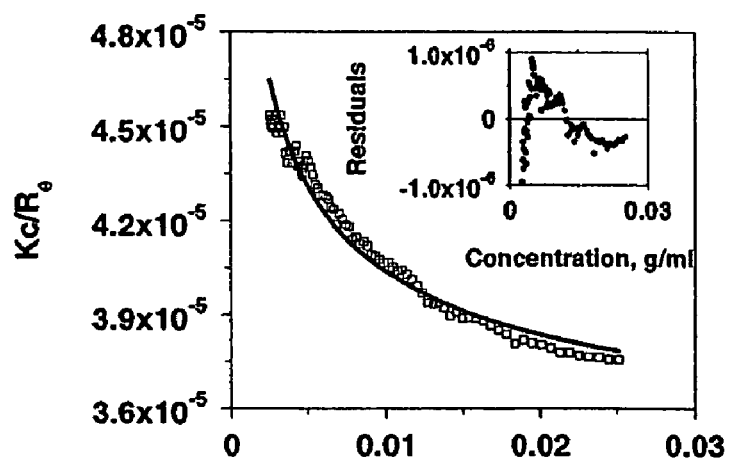
FIGS. 8A-8D are plots of $Kc/R_\Theta$ vs. concentration (g/ml).

Eq. 18 is a modified Debye equation that has been used to fit nonlinear Debye plots for the parameters, $K_D$ and $M_m$. The fitting was carried out by nonlinear least squares regression using Scientist software from Micromath (St. Louis, Mo.). FIG. 8A shows the fit of Eq. 18 to the nonlinear Debye plot obtained for βLg at pH 3.0 and 0.05 M NaCl solution concentration. As seen, the equation does not fit well to the curved Debye plot. This is further evident from the residuals (FIG. 8A, inset), which show that the data at low concentrations is under-predicted and that at higher concentrations is over-predicted by the equation. Thus, the association constant, $K_D$, is not by itself sufficient to fit the observed data, suggesting that the nonideality term may also have contributed to the observed curvature.

In view of this initial result, the nonideality term was included into the Debye Equation, i.e., Eq. 15 was used instead of simplified Eq. 16. Following the same derivation procedure as described above using Eq. 17 with inclusion of the B term, the following Debye equation is obtained.

$$\frac{Kc_t}{R_\theta} = \frac{(1 + 8K_D c_t/M_m)^{1/2} + 1}{2(1 + 8K_D c_t/M_m)^{1/2} M_m} + Bc_t \quad (19)$$

It is noted that Eq. 19 is similar to Eq. 18, with an additional term representing the first deviation from ideality. As discussed earlier, the term B represents all of the solute-solute interactions (monomer-monomer, monomer-dimer, dimer-dimer) present in solution. Eq. 19 was now used to fit the curved Debye plots for the parameters $K_D$, $M_m$ and B.

Figure 8B:
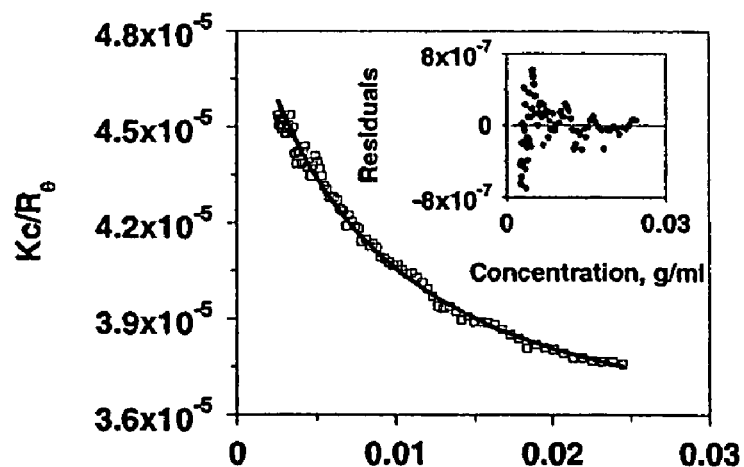
Figure 8C:
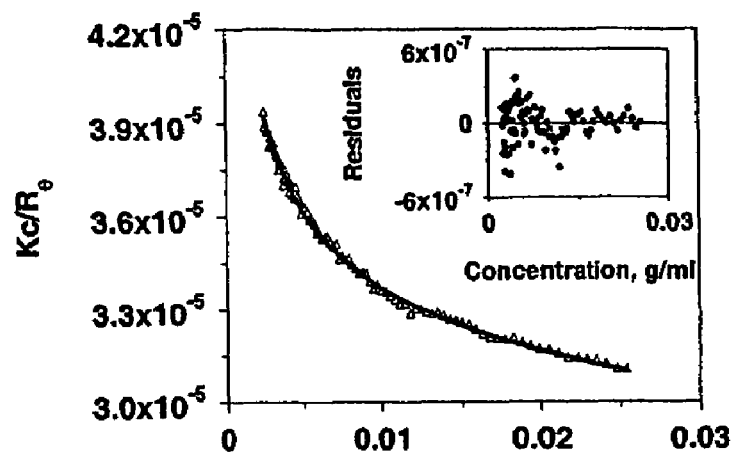
Figure 8D:
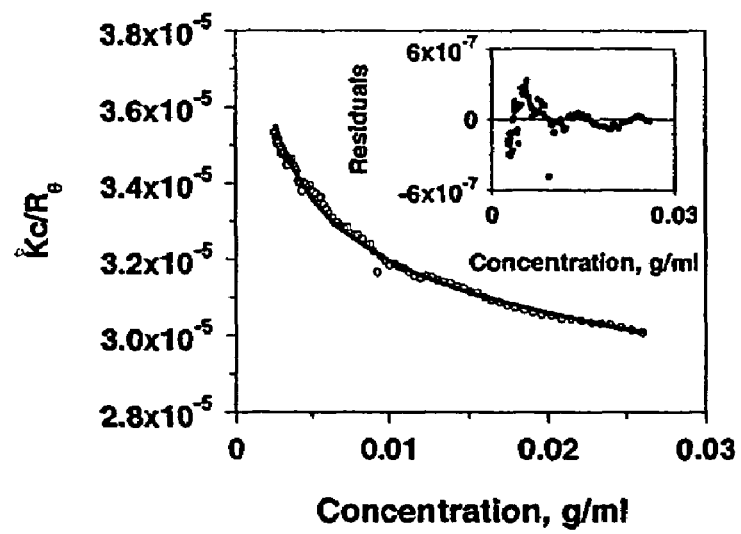

FIG. 8B shows the fit of Eq. 19 to the nonlinear Debye plots obtained for βLg at pH 3.0 for 0.05 M NaCl solution concentration. Clearly, this equation fits well to the data (compare FIG. 8B to FIG. 8A), as is also evident from the random distribution of the residuals (inset). Hence, the correction of the nonideality term is necessary for an accurate fit of the data. In fact, this has been observed across a range of investigated solution conditions. FIGS. 8C and 8D further demonstrate the viability of Eq. 19 for analysis of the data of βLg at pH 3.0 for 0.1 and 0.2 M NaCl solution concentrations. As observed, the equation fits well to the data with random distribution of the residuals. It is further notes that, although Eq. 18 did not fit well to the data (FIG. 8A), the theoretical line still lies close to the data points. Thus, the major contribution to the curvature still arises from the association of monomers to form dimers and the contribution of the nonideality term, although small, is important to attain an accurate fit of the data. Furthermore, the contribution of the nonideality term should only be considered as a correction term at this point, since a detailed mechanistic interpretation of B is much more complex in a multiple-species system.

The fitting yields $K_D$ values, molecular weight of the βLg monomer and B values. Table 2 summarizes these values for various solution conditions associated with βLg studies.

TABLE 2

Values of parameters obtained by analysis of the linear Debye plots (Eq. 1) and nonlinear Debye plots (Eq. 19) of β-lactoglobulin A and α-chymoytrypsin A for various solution conditions

| Solution Condition | $K_D$ (M$^{-1}$) | $M_m$ (Da) | $B_{22} \times 10^4$ (mol ml/g$^2$) |
|---|---|---|---|
| β-lactoglobulin A (20° C.) | | | |
| pH 2.3, (0 M NaCl) | —* | 18250 (±450)‡ | 8.5 (±0.5) |
| pH 3.0, 0.02 M NaCl | 1.44 (±1.05) × 10$^2$ | 19100 (±500) | 1.7 (±0.3) |
| pH 3.0, 0.05 M NaCl | 8.48 (±3.25) × 10$^2$ | 19900 (±320) | 0.8 (±0.1) |
| pH 3.0, 0.1 M NaCl | 4.62 (±0.63) × 10$^3$ | 18000 (±430) | −0.3 (±0.1) |
| pH 3.0, 0.2 M NaCl | 1.27 (±0.13) × 10$^4$ | 17500 (±450) | −0.3 (±0.1) |
| pH 3.0, 0.5 M NaCl | 1.08 (±0.32) × 10$^5$ | 18300 (±500) | −0.4 (±0.1) |
| pH 3.0, 1.0 M NaCl | —† | 37400 (±940) | −0.6 (±0.1) |
| α-chymotrypsin A (25° C.) | | | |
| pH 2.3, (0 M NaCl) | —* | 24900 (±860) | −0.8 (±0.1) |
| pH 4.12, 0.178 M NaCl | 1.25 (±0.55) × 10$^3$ | 25200 (±1020) | −0.2 (±0.1) |

TABLE 2-continued

Values of parameters obtained by analysis of the linear Debye plots (Eq. 1) and nonlinear Debye plots (Eq. 19) of β-lactoglobulin A and α-chymoytrypsin A for various solution conditions

| Solution Condition | $K_D$ (M$^{-1}$) | $M_m$ (Da) | $B_{22} \times 10^4$ (mol ml/g$^2$) |
|---|---|---|---|
| pH 4.12, 0.3 M NaCl | 4.36 (±0.81) × 10$^3$ | 25400 (±650) | 0.2 (±0.1) |
| pH 4.12, 0.5 M NaCl | 9.42 (±1.23) × 10$^3$ | 26000 (±1200) | 1.6 (±0.3) |

\*Primarily monomer present and
†Primarily dimer present; analysis was done using Eq. 1; all other solution conditions analyzed using Eq 19.
‡Number in the parenthesis represent the standard deviation, n = 3

It is evident that this method could track the $K_D$ values over three orders of magnitude ($10^2$-$10^5$ M$^{-1}$). It is noted that, even though the molecular weight of the βLg monomer is known, it is preferred to keep it as a floating parameter, since fixing this parameter did not result in good fitting of the data. For all solution conditions studied to date, the molecular weight thus obtained was always within 10% of that reported in literature. These results also advantageously indicate that the disclosed apparatus, system and method could be utilized without prior accurate knowledge of the protein molecular weight. It is important to note that flow rate did not affect the data and the parameters obtained after analysis, indicating that equilibrium is established fast between the monomer and the dimer species.

It can thus be concluded that rapid characterization (typically within a few hours) of protein self-association behavior can be achieved using the present apparatus, system and method. Such characterization is based on simultaneous measurement of protein concentration and scattered light intensity in flow-mode in conjunction with size-exclusion chromatography. The dependence of scattered light intensity on protein concentration shows a typical curvature for an associating system in the Debye plots that can be analyzed to yield association constants. The disclosed apparatus, system and method offer several advantages, including efficacious characterization of association behavior at moderately high concentrations (up to 25 mg/ml), no interference from irreversible aggregates or dust particles present in the sample, simple mathematical analysis and amenability to high throughput screening due to the use of the HPLC-based method.

Thus, the disclosed apparatus, systems and methods advantageously obtain desired measurements of properties associated with biomolecules, e.g., proteins, and in exemplary embodiments, permit simultaneous measurement of scattered light intensities and concentration, e.g., using a single flow cell. The measurements may be used to calculate the second viral coefficient, while simultaneously addressing issues associated with interdetector delay volume (IDV) and/or band-broadening. In exemplary embodiments, the disclosed apparatus, system and method permit for the measurement of the $B_{22}$ values of proteins in aqueous solutions, which systems and methods include the use of a dual-detector cell to simultaneously measure scattered light intensity and protein concentration in flow-mode after the protein elutes from a SEC column. It is believed that these systems and methods provide a reliable and simple means of estimating $B_{22}$ values, with results similar to those achieved by conventional techniques such as static light scattering.

Although the apparatus, systems and methods of the present disclosure have been described with reference to exemplary embodiments and implementations thereof, the present disclosure is not limited to or limited by such exemplary embodiments and/or implementations. Rather, the present disclosure is susceptible to various embodiments and/or implementations without departing from the spirit or scope of the present disclosure. For example, the apparatus, systems and methods of the present disclosure may be advantageously employed with high-pressure chromatography systems to separate impurities and/or simple syringe pumps to introduce sample(s) for analysis. Additional variations, modifications and/or enhancements to the disclosed apparatus, systems and methods may be made without departing from the spirit or scope of the present disclosure.

REFERENCES

Bloustine, J., V. Berejnov, and S. Fraden. 2003. Measurements of protein-protein interactions by size-exclusion chromatography, *Biophys. J.* 85:2619-2623.
Chi, E. Y., S. Krishnan, B. S. Kendrick, B. S. Chang, J. F. Carpenter, and T. W. Randolph. 2003a. Roles of conformational stability and colloidal stability in the aggregation of recombinant human granulocyte colony-stimulating factor. *Protein Sci.* 12:903-913.
Chi, E. Y., S. Krishnan, T. W. Randolph, and J. F. Carpenter. 2003b. Physical stability of proteins in aqueous solution: mechanism and driving forces in nonnative protein aggregation. *Pharm Res.* 20:1325-1336.
Curtis, R. A., J. Ulrich, A. Montaser, J. M. Prausnitz, and H. W. Blanch. 2002. Protein-protein interactions in concentrated electrolyte solutions: Hofmeister-series effects. *Biotech. Bioeng.* 79:367-380.
Fabian, H., L. P. Choo, G. I. Szendrei, M. Jackson, W. C. Halliday, L. Otvos, Jr., and H. H. Mantsch. 1993. Infrared spectroscopic characterization of Alzheimer plaques. *Appl. Spectosc.* 47:1513-1518.
George, A., Y. Chiang, B. Guo, A. Arabshahi, Z. Cai, and W. W. Wilson. 1997. Second viral coefficient as predictor in protein crystal growth. *Meth. Enzymol.* 276:100-110.
George, A., and W. W. Wilson. 1994. Predicting protein crystallization from a dilute solution property. *Acta Crystallog. D Biol. Crystallog.* D50:361-365.
Goo, B., S. Kao, H. McDonald, A. Asanov, L. L. Combs, and W. W. Wilson. 1999. Correlation of second viral coefficients and solubilities useful in protein crystal growth. *J. Crystal Growth.* 196:424-433.
Ho, J. G. S., A. P. J. Middelberg, P. Ramage, and H. P. Kocher. 2003. The likelihood of aggregation during protein renaturation can be assessed using the second viral coefficient. *Protein Sci.* 12:708-716.
Jackson, C., L M. Nilsson, and P. J. Wyatt. 1989. Characterization of biopolymers using a multi-angle light scattering detector with size-exclusion chromatography. *J. Applied Polym. Sci.* 43:99-114.
Knezic, D., J. Zaccaro, and A. S. Myerson. 2004. Thermodynamic properties of supernaturated protein solutions. *Crystal Growth Des.* 4:199-208.
Netopilik, M. 1997. Combined effect of interdetector volume and peak spreading in size exclusion chromatography with dual detection. *Polymers.* 38:127-130.
Netopilik, M. 2003. Problems connected with band-broadening in size-exclusion chromatography with dual detection. *J Biochem. Biophys. Meth.* 56:79-93.
Petsev, D. N., B. R. Thomas, S. T. Yau, and P. G. Vekilov. 2000. Interactions and aggregation of apoferritin molecules in solution: effects of added electrolytes. *Biophys. J.* 78:2060-2069.

Piazza, R. 1999. Interactions in protein solutions near crystallization: a colloid physics approach. *J Crystal Growth.* 196:415-423.

Poon, W. C. K. 1997. Crystallization of globular proteins. *Phys. Rev. E Stat. Phys. Plasmas Fluids Rel. Interdisc. Topics.* 55:3762-3764.

Rosenbaum, D. F., and C. F. Zukoski. 1996. Protein interactions and crystallization. *J. Crystal Growth.* 169:752-758.

Shortt, D. W. 1994. Measurement of narrow-distribution polydispersity using multiangle light scattering. *J Chromatogr. A.* 686:11-20.

Tanford, C. 1961. Physical Chemistry of Macromolecules. Wiley, N.Y.

Teske, C. A., H. W. Blanch, and J. M. Prausnitz. 2004. Measurement of lysozyme-lysozyme interactions with quantitative affinity chromatography. *J. Phys. Chem. B.* 108: 7437-7444.

Tessier, P. M., A. M. Lenhoff, and S. I Sandler. 2002. Rapid measurement of protein osmotic second viral coefficients by self-interaction chromatography. *Biophys. J.* 82:1620-1631.

Velev, O. D., E. W. Kaler, and A. M. Lenhoff. 1998. Protein Interactions in solution characterized by light and neutron scattering: comparison of lysozyme and chymotrypsinogen. *Biophys. J.* 75:2682-2697.

Wen, J., T. Arakawa, and J. S. Philo. 1996. Size-exclusion chromatography with on-line light-scattering, absorbance, and refractive index detectors for studying proteins and their interactions. *Anal. Biochem.* 240:155-166.

Wyatt, P. J. 1993a. Light scattering and the absolute characterization of macromolecules. *Anal. Chim. Acta.* 272:1-40.

Wyatt, P. J. 1993b. Mean square radius of molecules and secondary instrumental broadening. *J. Chromatogr. A.* 648:27-32.

Wyatt, P J., Wyatt Technology Corporation, USA, assignee. 2002. Method for measuring the 2nd viral coefficient of a protein monomer, U.S. Pat. No. 6,411,383.

Wyatt, P. J., and L. A. Papazian. 1993. The interdetector volume in modem light scattering and high performance size-exclusion chromatography. LC-GC. 11:862-872.

Zammit, M. D., T. P. Davis, and K. G. Suddaby. 1998. Factors influencing detector matching in multidetector SEC: solvent and concentration effects. *Polymers.* 39:5789-5798.

Zhang, J., and X. Y. Liu. 2003. Effect of protein-protein interactions on protein aggregation kinetics. *J Chem. Phys.* 119:10972-10976.

The invention claimed is:

1. A light scattering and detection apparatus, comprising:
a cell that is configured and dimensioned to accommodate a continuous solution flow through the cell;
first and second light sources interoperably coupled to the cell for directing respective first and second light beams associated with non-collinear first and second light transmission axes into the cell so as to pass through the solution flow;
a first light detector interoperably coupled to the cell for receiving and detecting light from the first light beam and passing along a third light transmission axis outward of the solution flow, the third light transmission axis being oriented at an angle relative to the first light transmission axis; and
a second light detector interoperably coupled to the cell for receiving and detecting light from the second light beam and passing along a fourth light transmission axis outward of the solution flow, the fourth light transmission axis being substantially linearly aligned with the second light transmission axis,
wherein the first and second light detectors are positioned and oriented to allow for simultaneous measurements by the first and second light detectors of substantially a same region of the solution flow.

2. A light scattering and detection apparatus according to claim 1, wherein the first and third light transmission axes are oriented at an obtuse angle relative to each other.

3. A light scattering and detection apparatus according to claim 2, wherein the obtuse angle at which the first and third light transmission axes are oriented relative to each other has an extent of approximately one-hundred and sixty-five degrees.

4. A light scattering and detection apparatus according to claim 1, wherein the first and third light transmission axes are oriented at an angle to each other having an extent of approximately ninety degrees.

5. A light scattering and detection apparatus according to claim 1, further comprising a third light detector interoperably coupled to the cell for receiving and detecting light from the first light beam and passing along a fifth light transmission axis outward of the solution flow, the fifth light transmission axis being oriented at an angle relative to the first light transmission axis.

6. A light scattering and detection apparatus according to claim 5, wherein the first and fifth light transmission axes are oriented at an obtuse angle relative to each other.

7. A light scattering and detection apparatus according to claim 6, wherein the obtuse angle at which the first and fifth light transmission axes are oriented relative to each other has an extent of approximately one-hundred and sixty-five degrees.

8. A light scattering and detection apparatus according to claim 1, wherein the cell further includes a sample inlet that is configured and dimensioned so as to permit the cell to interoperably couple to a size-exclusion chromatography (SEC) column and thereby receive a continuous flow of solution eluting therefrom.

9. A light scattering and detection apparatus according to claim 1, wherein the cell further includes a sample outlet sized and shaped so as to permit the cell to discharge a continuous solution flow received from an size-exclusion chromatography (SEC) column.

10. A light scattering and detection apparatus according to claim 1, wherein the second and fourth light transmission axes are oriented at an angle relative to the first light transmission axis.

11. A light scattering and detection apparatus according to claim 10, wherein the angle at which the second and fourth light transmission axes are oriented relative to the first light transmission axis has an extent of approximately ninety degrees.

12. A light scattering and detection apparatus according to claim 1, wherein the second light source is an ultraviolet light source, and the second detector is adapted to measure a concentration of a substance associated with the solution flow.

13. A light scattering and detection apparatus according to claim 1, wherein the first light source is a laser light source, and the first detector is adapted to measure a scattered light intensity associated with the solution flow.

14. A light scattering and detection apparatus according to claim 1, wherein the solution flow comprises a biomolecular solution.

15. A light scattering and detection apparatus according to claim 1, wherein the solution flow is a protein solution.

16. A light scattering and detection apparatus according to claim 15, wherein protein concentration and light scattering measurements are made with respect to the solution flow, and wherein such measurements are used to calculate at least one second viral coefficient ($B_{22}$) value for a protein in the solution flow.

17. A method of light scattering and detection, comprising:
 directing a continuous flow of a solution into and through a sample cell;
 passing first and second light beams into the solution within the sample cell such that the first and second light beams substantially intersect within the solution;
 measuring a scattered light intensity of the solution via light detected from the first light beam; and
 measuring a concentration of a substance in the solution via light detected from the second light beam,
 wherein the measuring a scattered light intensity step and the measuring a concentration step are performed substantially simultaneously and are of substantially a same region of the solution flow.

18. A method of light scattering and detection according to claim 17, wherein the solution is a protein solution.

19. A method of light scattering and detection according to claim 18, wherein the measuring a concentration includes measuring a concentration of a protein in the protein solution, the method further comprising calculating at least one second viral coefficient ($B_{22}$) value for the protein based on the measurements of scattered light intensity and protein concentration.

20. A dual detector cell, comprising:
 a cell;
 a first light source interoperably coupled to the cell to direct a first light beam into the cell;
 a first detector interoperably coupled to the cell to detect light from the first light beam;
 a second light source interoperably coupled to the cell to direct a second light beam into the cell; and
 a second detector interoperably coupled to the cell to detect light from the second light beam;
 wherein light is simultaneously detected by the first and second detectors and is used to simultaneously measure (i) a light scattering intensity of a continuous solution flow into and through the cell, and (ii) a concentration of a substance in the continuous solution flow into and through the cell, wherein the simultaneous measurements are of substantially a same region of the solution flow.

* * * * *